(12) United States Patent
Nagai

(10) Patent No.: US 6,192,735 B1
(45) Date of Patent: Feb. 27, 2001

(54) THREE-DIMENSIONAL POSITION CALIBRATOR

(75) Inventor: Hiroshi Nagai, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 0 days.

(21) Appl. No.: 09/213,889

(22) Filed: Dec. 17, 1998

(30) Foreign Application Priority Data

Dec. 17, 1997 (JP) .................................................. 9-348090

(51) Int. Cl.[7] .................................................. G01N 29/26
(52) U.S. Cl. ........................ 73/1.82; 73/1.86; 73/866.5
(58) Field of Search .................................. 73/1.82, 1.86, 73/1.79, 866.5, 865.8

(56) References Cited

U.S. PATENT DOCUMENTS

| | | | |
|---|---|---|---|
| 4,430,883 | | 2/1984 | Auphan .................................. 73/1.83 |
| 4,476,549 | * | 10/1984 | Dragonette et al. .................. 73/1.86 |
| 4,567,896 | * | 2/1986 | Barnea et al. .......................... 73/1.86 |
| 4,660,419 | * | 4/1987 | Derkacs et al. ........................ 73/1.82 |
| 5,574,212 | * | 11/1996 | Madsen et al. ........................ 73/1.82 |
| 5,665,893 | * | 9/1997 | Smith ..................................... 73/1.82 |
| 5,827,942 | * | 10/1997 | Madsen et al. ........................ 73/1.82 |

OTHER PUBLICATIONS

TOMTEC Imaging Systems GmbH, Oct. 1996, Release 1.0, pp. 1–15, "Freehand Scanning Device Installation and Service Manual".

* cited by examiner

Primary Examiner—Hezron Williams
Assistant Examiner—Michael Cygan
(74) Attorney, Agent, or Firm—Sughrue, Mion, Zinn, Macpeak & Seas, PLLC

(57) ABSTRACT

A probe 12 is correctly fixed to a calibrator body 1, and the calibrator body 1 is mounted on the base stand 22. With the surfaces thereof abutted against a block 14, and it is positioned in X-axis, Y-axis and Z-axis directions. Under this condition, image data is calibrated which is provided with the aid of an ultrasonic wave generated by the probe according to the spatial position data of the magnetic field receiver 27.

12 Claims, 7 Drawing Sheets

THREE-DIMENSIONAL POSITION CALIBRATOR

BACKGROUND OF THE INVENTION

1. Field of the Invention

This invention relates to a three-dimensional position calibrator which is adapted to correct the three-dimensional position of a probe provided for equipment adapted to transmit and receive an ultrasonic wave to detect an echography of an object under test.

2. Related Art

A probe an provided for an ultrasonic inspecting equipment and generating an ultrasonic wave is provided with a magnetic field receiver which receives a magnetic field generated by a magnetic transmitter in order to detect the three-dimensional spacial position coordinate. The magnetic field receiver is fixed to the probe with adhesive as a single unit. Hence, the magnetic field receiver mounting position is not constant, so that image data inputted to the computer is inaccurate.

SUMMARY OF THE INVENTION

In view of the foregoing, an object of the invention is to provide a three-dimensional position calibrator, which utilizes an ultrasonic wave to provide correct image data.

The foregoing object has been achieved by the present invention, to calibrate a spatial position coordinate by receiving a magnetic field transmitted from a magnetic field transmitter with a magnetic field receiver mounted on a probe, there is provided a three-dimensional position calibrator comprising:

a calibrator on which said probe is mounted;

fixing means for fixedly positioning said probe at a predetermined position on the calibrator; and positioning means for positioning said probe in triaxial directions different to one another.

When the calibrator of the present invention is used, a magnetic field receiver is attached on the probe. Next, the probe is fixed on a predetermined position of the calibrator by the positioning means in triaxial directions in turn. Thus, the spacial position of the magnetic field receiver is measured in each direction. Next, the relationship between the spacial position of the magnetic field receiver and an ultrasonic scanning surface scanned by the probe is obtained in view of the relationship between the spatial virtual center and the measured spacial positions of the magnetic field receiver.

According to a second aspect of the present invention, the calibrator has a reference target, which is picked up by the probe as a spatial virtual center. When the calibrator is positioned in triaxial directions by the positioning means, the spatial virtual center is spatially matched in each direction.

According to a third aspect of the present invention, the positioning means positions the calibrator in triaxial directions that are orthogonal to one another.

According to a fourth aspect of the present invention, the calibrator includes an axis reference target for confirming whether or not the probe is positioned in a predetermined direction by ultrasonic image.

DETAILED DESCRIPTION OF THE PREFERRED EMBODIMENTS

An example of a three-dimensional position calibrator, which constitutes an embodiment of the invention, will be described with reference to the accompanying drawings. The embodiment is described in brief as follows: When a probe adapted to transmit and receive an ultrasonic wave generated by an ultrasonic diagnostic equipment is set in triaxial directions, the spatial position coordinate of a magnetic field receiver which is mounted on the probe and receives a magnetic field, is detected, and the spatial position of the echo image of an object under test, which is provided by the ultrasonic diagnostic equipment, is corrected so that a correct three-dimensional image is formed again.

Figure 1:
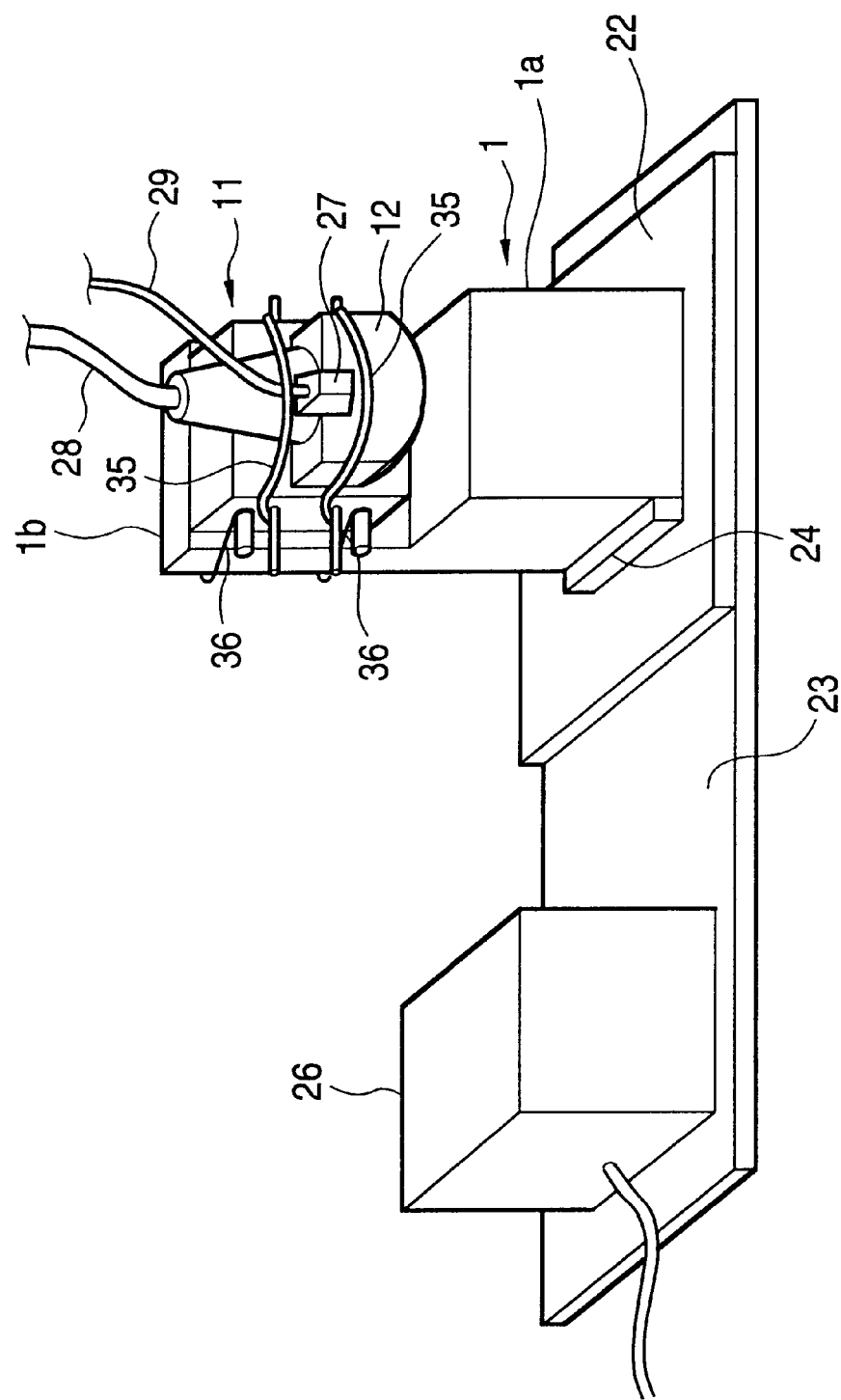
FIG. 1 is a perspective view showing the whole arrangement of a three-dimensional position calibrator, which is an embodiment of the invention.
Figure 2:
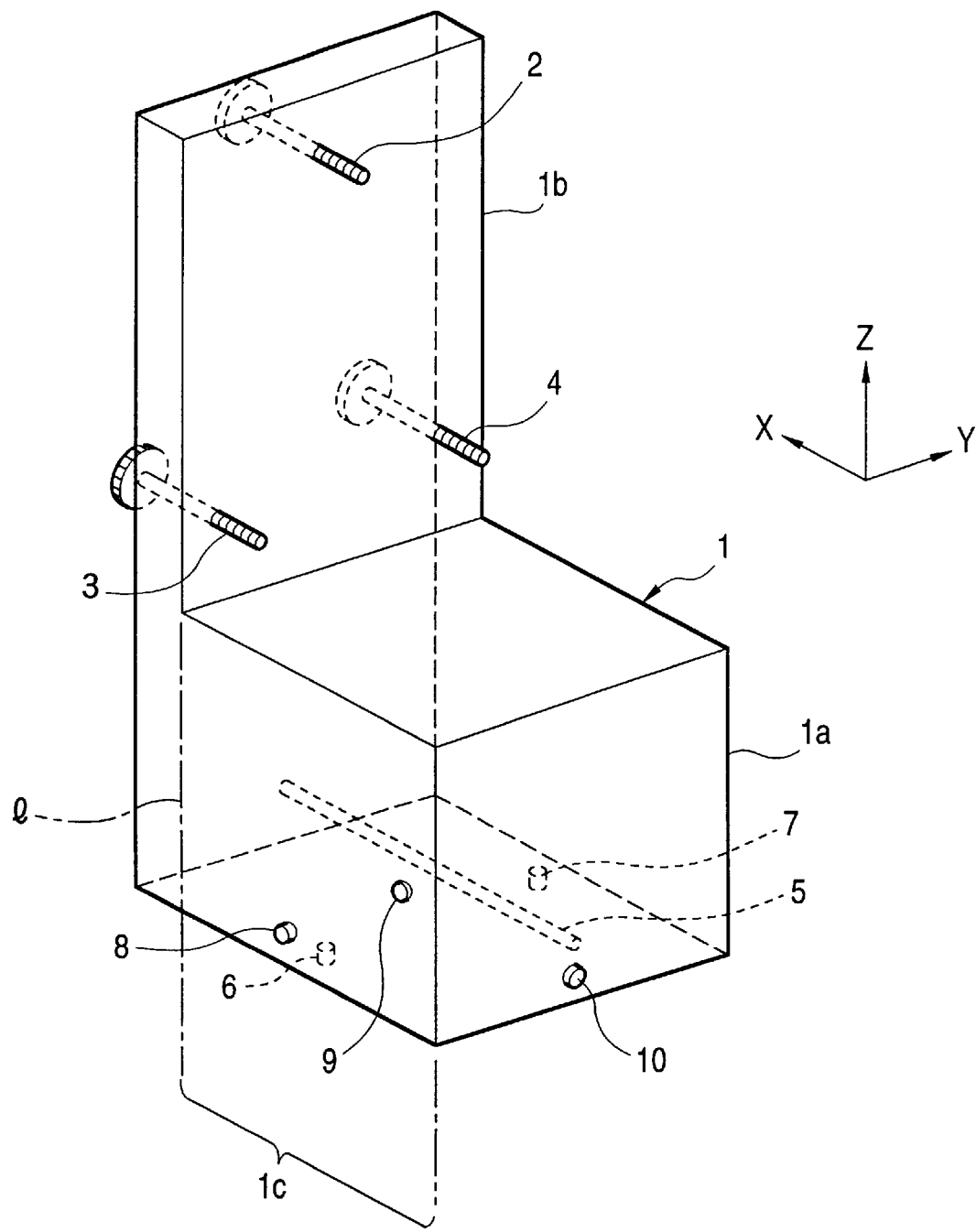
FIG. 2 is a perspective view showing the arrangement of a calibrator body shown in FIG. 1.
Figure 3:
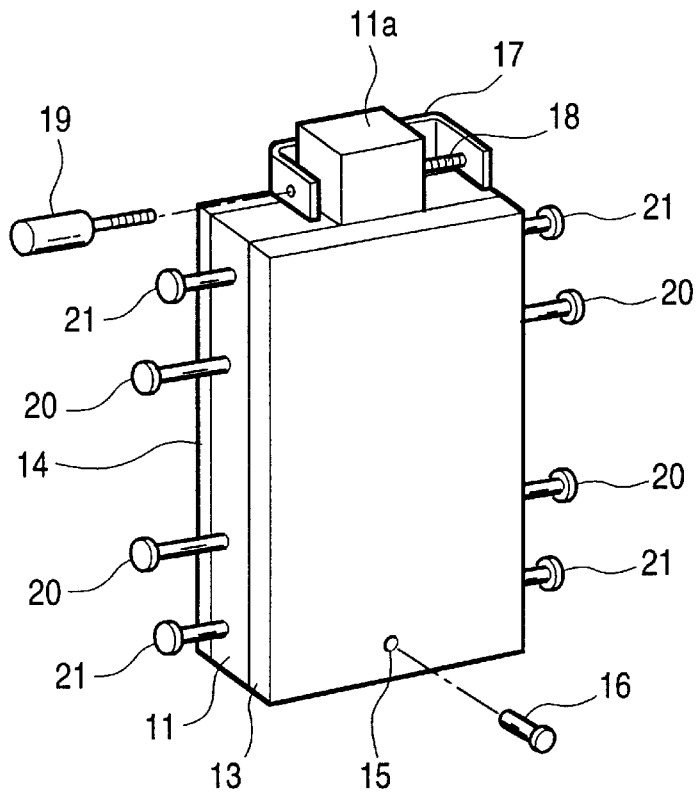
FIG. 3 is a perspective view showing the arrangement of a probe mounting board shown in FIG. 1.
Figure 4:
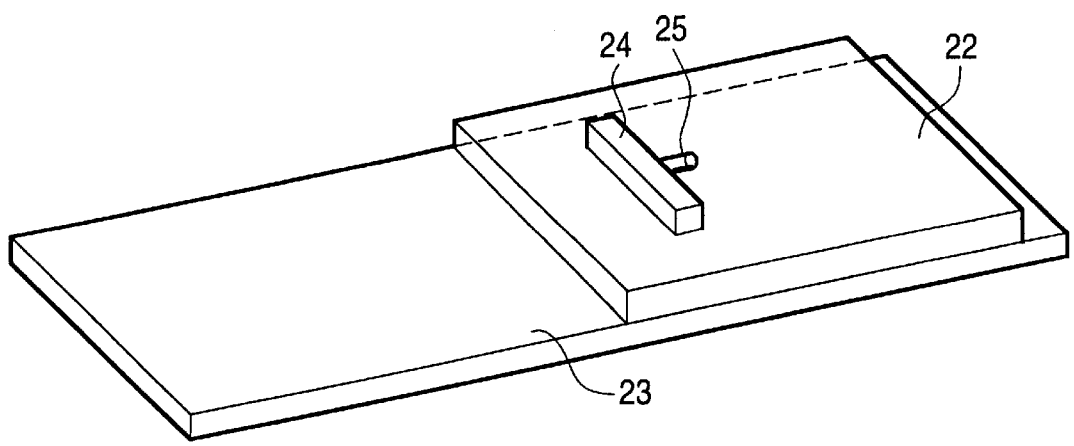
FIG. 4 is a perspective view showing the arrangement of a base stand shown in FIG. 1.

FIG. 1 is a perspective view showing the whole arrangement of a position calibrator. FIG. 2 is a perspective view showing a calibrator body shown in FIG. 1. FIG. 3 is a perspective view showing a probe mounting board shown in FIG. 1. FIG. 4 is a perspective view showing a base stand shown in FIG. 1.

In FIG. 2, the calibrator body 1 is L-shaped and made of acrylic resin. Its lower section 1a has the shape of a rectangular box having parallelogram faces; however it is of a cube 1c up to an auxiliary line. A probe mounting section 1b is extended from one side of the lower section 1a, and three adjusting screws 2, 3 and 4 are screwed into the probe mounting section 1b from outside. An elongated-hole-shaped reference target 5 is formed in the lower section 1a at a predetermined height from the bottom surface of the lower section 1a in such a manner that it is in parallel with the bottom surface and at the center as viewed in the direction of width of the probe mounting section 1b and perpendicular to the probe mounting section 1b. Furthermore, a pair of axial reference targets 6 and 7 are provided on the bottom of the lower section 1a in such a manner that they are located at the same distance from the probe mounting section 1b, and at the middle of the cube 1c as viewed in the direction of X-axis, and on both sides of the reference target 5. Furthermore, on one side surface of the lower section 1a which is perpendicular to the probe mounting section 1b, holes 8 and 9 are provided which, when the calibrator body is mounted on the base stand (described later), are used for the positioning work in an X-axis direction and in a Z-axis direction. Similarly, on the side surface of the lower section 1a which confronts with the probe mounting section 1b, a hole 10 is formed which is used for the positioning work in the Y-axis direction.

As shown in FIG. 3, a rubber plate 13, which prevents a probe 12 (shown in FIG. 1) from being shifted while at the same time, protecting the probe 12, is mounted on the front surface of a probe mounting board 11 which is rectangular and formed with acrylic resin. A rectangular-plate-shaped aluminum plate 14 is mounted on the rear surface of the probe mounting board 11. In the center of the lower portion of the aluminum plate 14, a screw 16 is screwed which loosely penetrates the rubber plate 13 and a hole 15 formed in the center of the lower portion of the probe mounting board 11. A protrusion section 11a is integrally mounted on an upper portion of the probe mounting board 11 in such a manner that it is located at the center thereof. A U-shaped bracket 17, which surrounds the protrusion section 11a, is mounted on the upper portion of the aluminum plate 14. A coil spring 18 is set between the protrusion section 11a and one side of the bracket 17, and a screw 19 is screwed in the other side of the bracket 17. As the screw 19 is turned, the protrusion section 11a is pushed against the elastic force of the coil spring 18, so that the probe mounting board 11 is turned about the screw 16. On each of the two side surfaces of the probe mounting board 11, two probe mounting pins 20 and two probe mounting board fixing pins 21 are provided.

As shown in FIG. 4, the base stand 22 supporting the calibrator body 1 is fixed to one side of a rectangular-plate-shaped base board 23, and a block 24, which abuts against one surface of the calibrator body 1, is fixedly mounted on the base board 22. The block 24 has a positioning ping 25 on one surface wherein the positioning ping 25 is engaged with any one of the holes 8, 9 and 10 formed in the surfaces of the calibrator body 1.

The probe 12 has a transducer (not shown) in a semi-circular housing as shown in FIG. 1, and an echo signal which is obtained when an ultrasonic is wave generated by the transducer and is reflected by striking an object under test, is detected by the transducer. A magnetic field receiver 27, adapted to receive a magnetic field generated by a magnetic field transmitter 26 mounted on the base board 23, is fixedly mounted on the front surface of the probe 12. The probe 12 is connected to one end of a cable 28 which drives the transducer to transmit an echo signal. The other end of the cable 28 is connected to an ultrasonic diagnostic equipment (not shown). The magnetic field receiver 27 is connected to a cable 29. The magnetic field receiver 27 receives a magnetic field generated by the magnetic field transmitter 26, detects spatial position coordinates with respect to the magnetic field receiver 27, and applies those data to a magnetic field controller (not shown) via cable 29.

Figure 5:
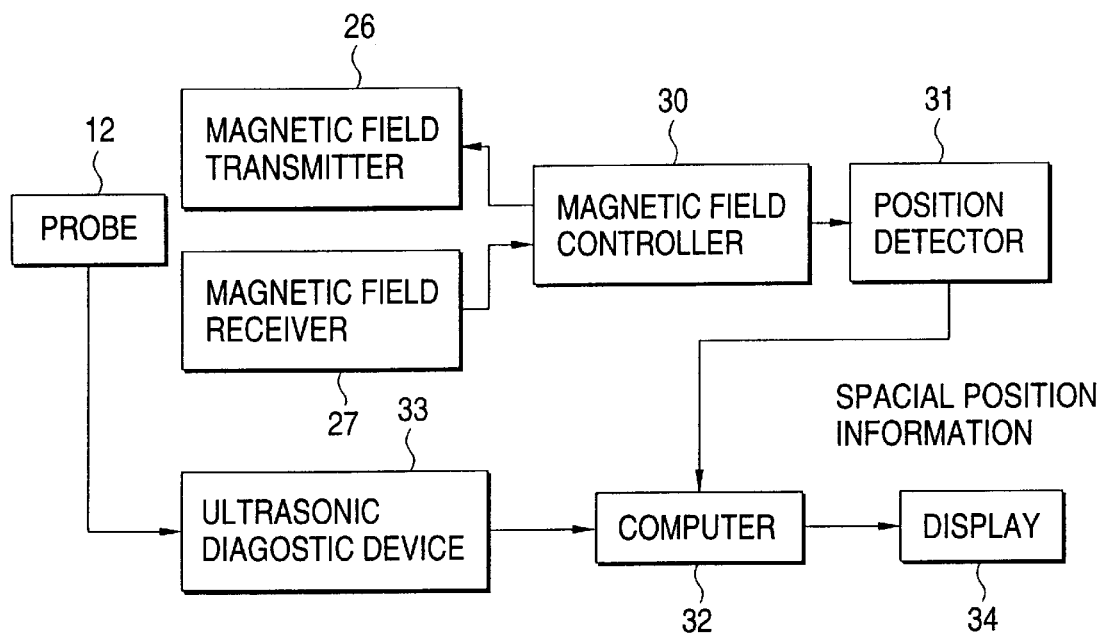
FIG. 5 is a block diagram for a description of the function of the embodiment of the invention.

FIG. 5 is a functional block diagram showing the above-described arrangement of the three-dimensional position calibrator. The magnetic field transmitter 26 generates a magnetic field in response to a signal outputted by the magnetic controller 30. The magnetic field receiver 27 detects the magnetic field thus generated to obtain the three-dimensional position coordinate data of the magnetic field receiver 27. The data is applied through the magnetic field controller 30 to the position detector 31, and the spatial position of the receiver 27 is detected by the position detector 31. This spatial position data is applied to a computer 32. On the other hand, the ultrasonic image which the probe 12 detects with the aid of the ultrasonic wave is applied through the ultrasonic diagnostic equipment 33 to the computer 32. The latter 32 corrects the image data according to the aforementioned spatial position data of the receiver 27, forms a cubic image, and displays it as a three-dimensional image on a display 34.

A process of correction with the three-dimensional position calibrator according to the embodiment will be described with reference to the accompanying drawings.

Figure 8:
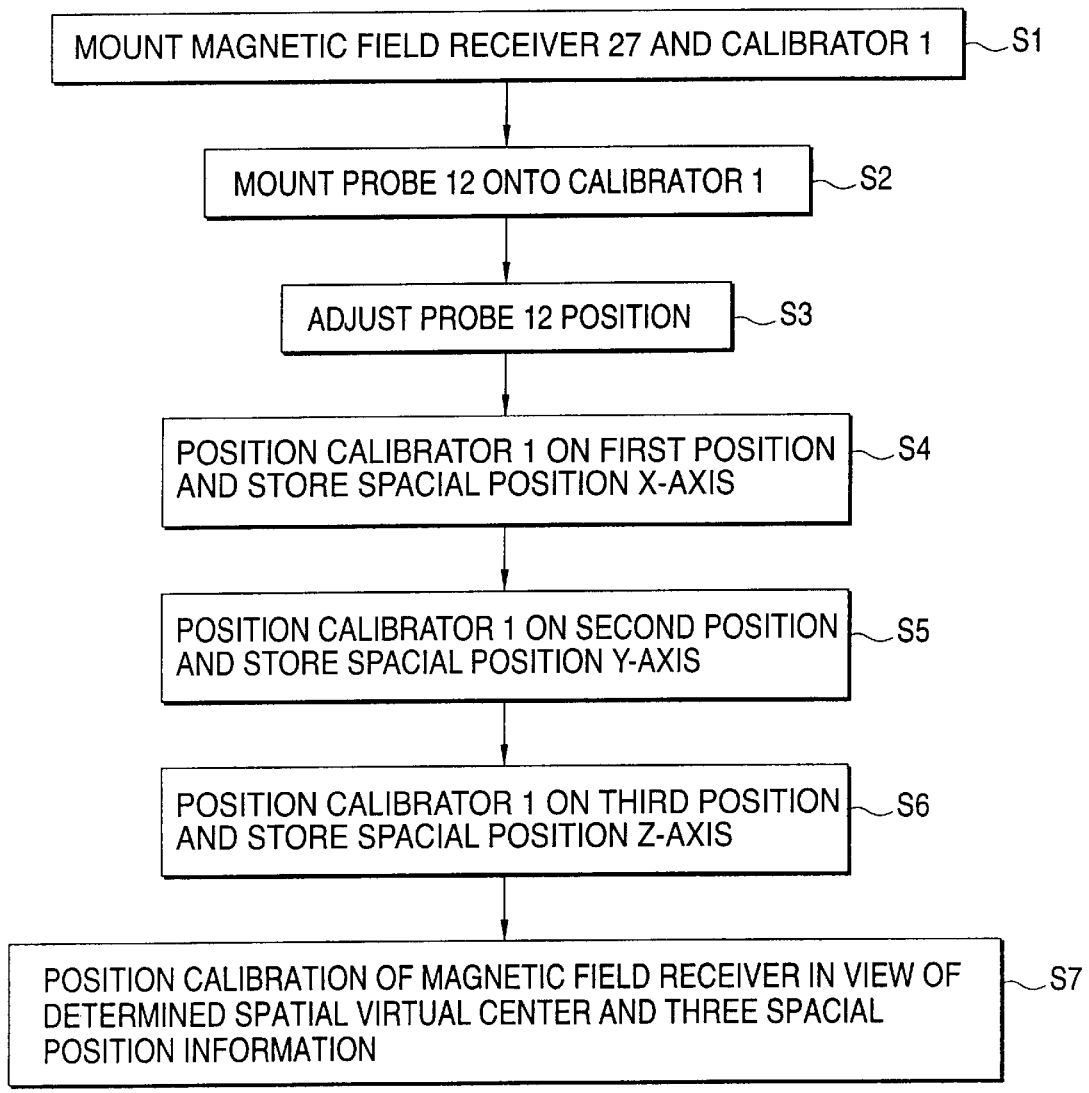
FIG. 8 is showing a flow chart for calibration processing operation according to the present invention.

As shown in FIG. 8, first of all, the magnetic field receiver 27 and the calibrator body are set (step S1), the probe 12 is mounted on the calibrator body 1 (step 2). When the probe 12 is mounted on the calibrator body 1, the probe 12 is fixed to the probe mounting board 11 with the rubber band 35. In this case, the rubber band 35 is elastically laid over the pins 20 provided on both sides of the probe mounting board 11. Next, the probe mounting board 11 is secured to the upper portion of the calibrator body 1 with a rubber band 36. In this case, the rubber band 36 is elastically laid over the pins 21.

Figure 6:
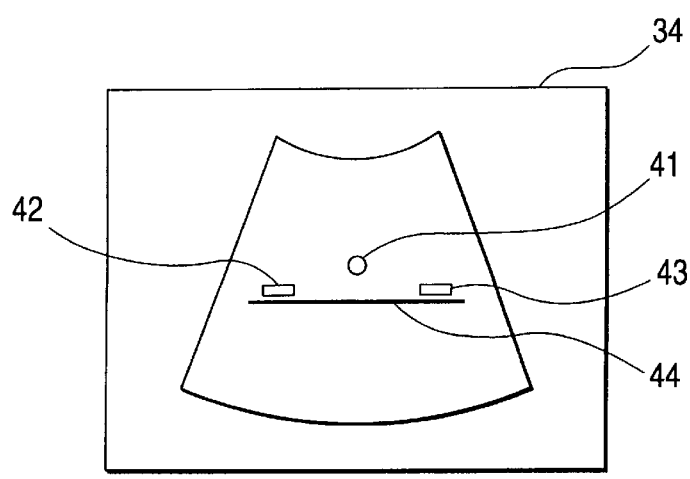
FIG. 6 is an explanatory diagram showing an example of an image which is displayed on a display shown in FIG. 5.

Next, the probe position is finely corrected with respect to the calibrator body 1 (step 3). This correction is performed such that the screws 2, 3, 4, 19 are turned to correct the angle of the probe mounting board 11 with respect to the calibrator body 1 so that the ultrasonic wave generated by the probe 12 is adjusted until the echo image which reflects striking against the reference target 5 and the axial reference targets 7 is clearly displayed on the display 34 as shown in FIG. 6. In FIG. 6, reference numeral 41 designates the echo image of the reference target 5; 42 and 43, the echo images of the axial reference targets, respectively; and 44, the echo image of the bottom surface of the calibrator body 1. If the probe 12 is not mounted in a direction which is correct with respect to the calibrator 1, the echo image may be diminished or become foggy.

According to this embodiment, the calibrator 1 is made of acrylic resin. The ultrasonic speed while passing through acrylic resin is different from the ultrasonic speed while passing through a living tissue. Namely, the ultrasonic speed while passing through acrylic resin (about 2700 m/s) is faster than the ultrasonic speed while passing through a living tissue (about 1500 m/s).

Thus, in consideration of this speed difference, the reference target 5 is provided near the bottom portion of a lower portion 1a of the calibrator 1, and the echo image 41 is displayed on the center of the display 34. Namely, the echo image of the reference target 5 is displayed on the same position of an echo image of the center of lower portion 1a of a cube 1c obtained when the ultrasonic speed is converted to the internal ultrasonic speed of the living tissue on the echography. Thus, the time taken for reaching the center of the cube 1c at internal ultrasonic speed of living tissue and time taken for reaching the reference target 5 at internal ultrasonic speed acrylic resin are the same.

In this embodiment, a spatial virtual center P corresponds to the center of the cube 1c located on a predetermined position of the base stand 22. A coordinate of the spatial virtual center is already known, because a size of the cube 1c is already known. The positions of the magnetic field receiver 27 and the calibrator 1 are to be located on the base stand 22.

Figure 7:
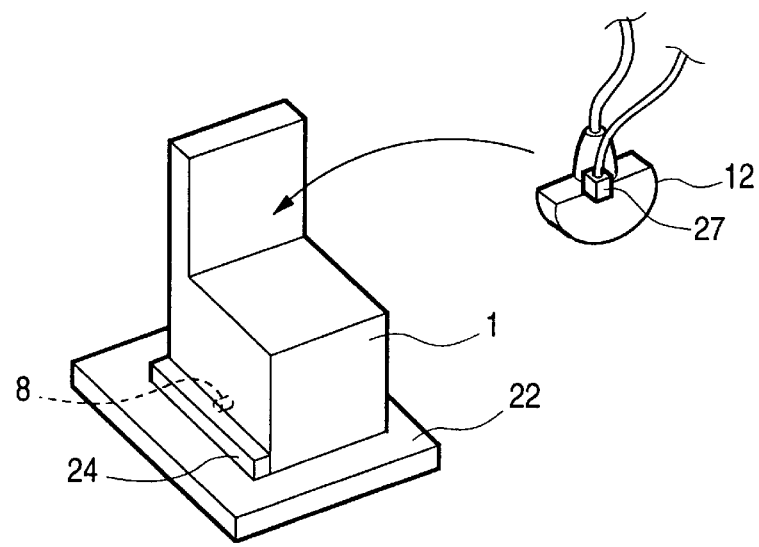
FIGS. 7(a), (b) and (c) are perspective diagrams for a description of the mounting of the calibrator body (FIG. 1) on the base stand in triaxial directions.
Figure 7:
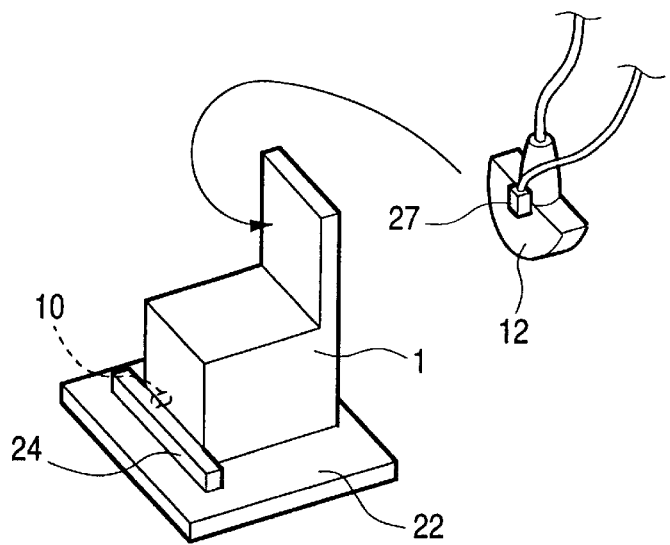
Figure 7:
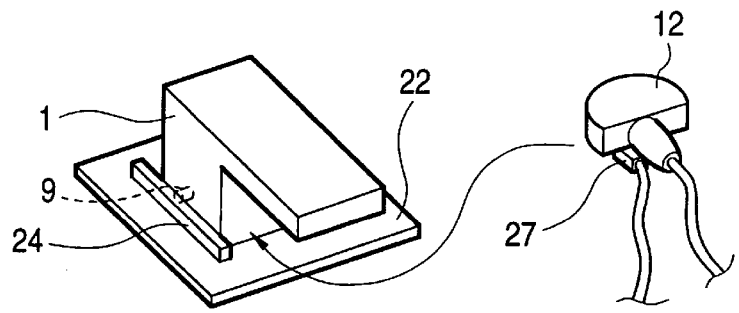

Next, the calibrator 1 is positioned on a first position by the operator, and the position detector 31 measures a spacial position coordinate of the magnetic receiver 27. This data is inputted and stored into the computer 32 (step 4). As shown in FIG. 7(a), the meaning that the calibrator 1 is positioned on the first position is that a side surface of the calibrator 1 in X-axis is brought into contact with the block 24 and the pin 25 is fitted on the hole 8 provided on the side surface of the block 24. Next, the operator takes to position the calibrator 1 to a second position, and the position detector 31 measures a spacial position coordinate of the magnetic receiver 27. These data is inputted and stored into the computer 32 (step 5). As shown in FIG. 7(b), the meaning that the calibrator 1 is positioned on the second position is that a side surface of the calibrator 1 in Y-axis is brought into contact with the block 24, and the pin 25 is fitted on the hole 10 provided on the side surface of the block 24.

Next, the calibrator 1 is positioned on a third position by the operator, and the position detector 31 measures a spacial position coordinate of the magnetic receiver 27. This data is inputted and stored into the computer 32 (step 6). As shown in FIG. 7(c), the meaning of the calibrator 1 positioned on the third position is that a side surface of the calibrator 1 in Z-axis is brought into contact with the block 24, and the pin 25 is fitted on the hole 9 provided on the side surface of the block 24.

As described above, the calibrator 1 is positioned on the base stand 22 in triaxial directions which are perpendicular to one another, and the spacial position coordinate of the magnetic receiver 27 is measured and stored in each state.

Figure 9:
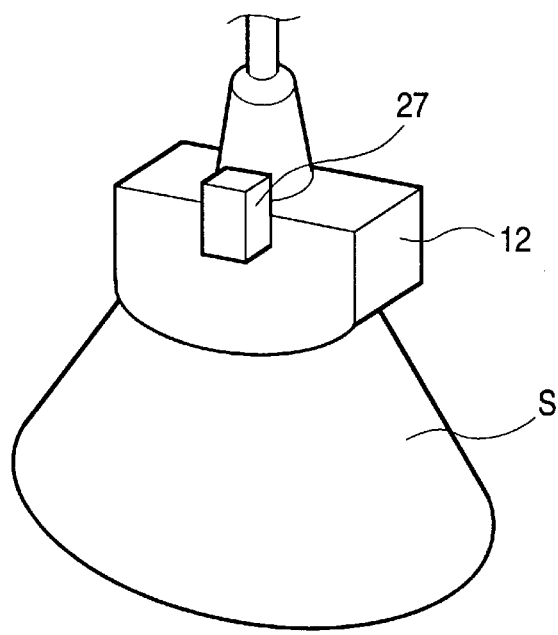
FIG. 9 is showing the position relationship of the magnetic field receiver and an ultrasonic scanning surface S scanned by the probe.
Figure 10:
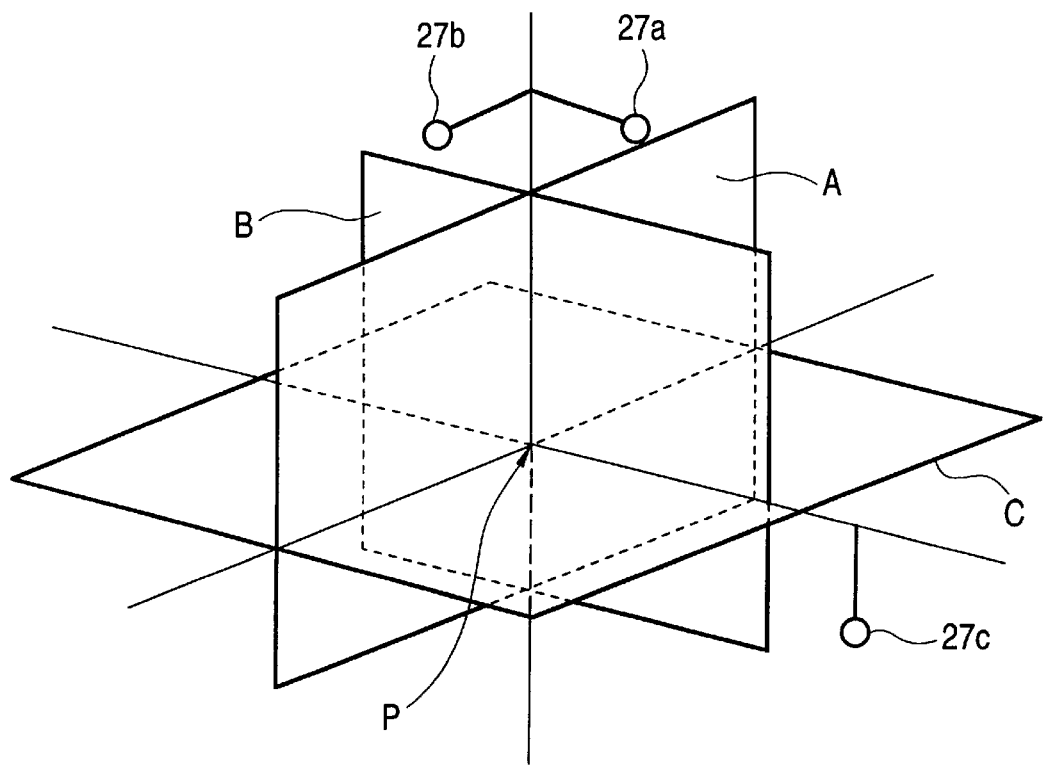
FIG. 10 is showing the position relationship of three positions of the magnetic field receiver and the reference surfaces which are passing through the spatial virtual center, according to the present invention.

Next, the computer 32 performs the position calibration of the magnetic field receiver 27 on the basis of three spacial position information's and the determined spatial virtual center (step 7). FIG. 9 is showing the position relationship of the magnetic field receiver 27 and an ultrasonic scanning surface S scanned by the probe 12. FIG. 10 is showing the position relationship of three positions 27a, 27b and 27c of the magnetic field receiver 27 and the reference surfaces A, B and C which are passing through the spatial virtual center.

The measured positions 27a, 27b and 27c of the magnetic field receiver 27 are changed in view of a mounting position of the magnetic field receiver 27. However, upon the measurement of the positions 27a, 27b and 27c, there is obtained the positional relationship of the magnetic field receiver 27 and the ultrasonic scanning surface scanned by the probe 12. Thus, when the spacial position of the magnetic field receiver 27 is measured, the spacial position of the ultrasonic scanning surfaced scanned by the probe 12 is calibrated.

As was described above, the operator correctly sets the probe on the calibrator body 1 with reference to the image, and sets the calibrator body I on the base stand 22 in the X-axis, Y-axis and Z-axis directions, so that the spatial position coordinate data of the magnetic field receiver 27 is obtained. And as shown in FIG. 5, the data is processed with the computer 32, whereby the spatial position is calibrated with respect to the ultrasonic image. With the probe which has been calibrated in the above-described manner, an echography of living tissue and accurate spacial position information of the ultrasonic scanning surface scanned by the probe 12 are simultaneously obtained so that an accurate three dimensional image could be indicated on the display 34.

According to this embodiment, when the calibrator is positioned in three different directions from one another, triaxial directions are perpendicular to one another. However, under condition that the triaxial directions are perpendicular to one another in the same plane, any three directions could be available. Further, when each spacial position is expressed in this embodiment, there is obtained the coordinate employing coordinate axes as three directions described above. However, any coordinate could be employed by using coordinate axes having the three directions which are different such as a polar coordinate or the like.

The present invention is not limited by the calibrator made of acrylic resin. However, the position of the reference target should be determined in view of the ultrasonic speed passing through the material. Further, in this embodiment, a pair or axial reference targets 6 and 7 is provided on one surface of the calibrator. Of course, it is applicable for employing additional reference targets in such a manner that the additional reference targets are provided on a surface opposite to the surface having a pair of axial reference targets. In this structure, it is possible to position the probe on a predetermined position more accurately and quickly.

Additionally, in this embodiment, rubber band 35 is used for positioning the probe 12 on the calibrator body 1. Instead, it is possible to use a surface fastener or hook to perform the same function. Also, the spatial virtual center is positioned at center of cube 1a. However, it is not necessary to employ a cube as long as the spatial virtual center is set on the same spatial point.

As was described above, in the three-dimensional position calibrator of the invention, the probe to which the magnetic field receiver is fixed and which generates an ultrasonic wave is fixedly positioned at a predetermined position on the calibrator body, and the calibrator body is positioned on the base stand in triaxial directions which are different to one another, so that the image data, which is detected by the probe is calibrated according to the spatial position data of the magnetic field receiver in various postures. Hence, the image data can be calibrated with ease.

According to a second aspect of the present invention, the calibrator has a reference target, which is picked up by the probe as a spatial virtual center. When the calibrator is positioned in triaxial directions by the positioning means, the spatial virtual center is spatially matched in each direction. Thus, the operation for calibration of an image information and data processing are easily handled.

According to a third aspect of the present invention, the positioning means positions the calibrator in triaxial directions that are orthogonal to one another. As a result, the shape of the calibrator is in simple so that it can be easily manufactured.

According to a fourth aspect of the present invention, the calibrator includes an axis reference target for confirming whether or not the probe is positioned on a predetermined direction by ultrasonic image. Thus, it is possible to position the probe on a predetermined position with respect to the calibrator, more accuracy and quickly.

What is claimed is:

1. A three-dimensional position calibrator for calibrating spatial position coordinates by receiving a magnetic field transmitted from a magnetic field transmitter with a magnetic field receiver mounted on a probe comprising:

a calibrator on which said probe is mounted;

fixing means for fixedly positioning said probe at a predetermined position on the calibrator; and positioning means for positioning said probe in triaxial directions.

2. A three-dimensional position calibrator as claimed in claim 1, wherein said calibrator has a reference target imaged as a spatial virtual center by said probe, and when said probe is positioned in triaxial directions, said spatial virtual center is set on the spatially same point in each measured position in view of the direction.

3. A three-dimensional position calibrator as claimed in claim 1, wherein said positioning means positions said probe in triaxial directions perpendicular to one another.

4. A three-dimensional position calibrator as claimed in claim 1, wherein said calibrator includes an axis reference target for confirming whether said probe is positioned in a predetermined direction by ultrasonic detection of said axis reference target.

5. A method for calibrating spatial position coordinates with the three-dimensional position calibrator according to claim 1, comprising the steps of:

fixing said probe and said magnetic field receiver to said calibrator, via said fixing means, at a predetermined position on said calibrator;

positioning said probe in triaxial directions;

obtaining spatial position information from said magnetic field receiver coresponding to each axial direction in which said probe is positioned; and calibrating a spatial position coordinate on the basis of obtained spatial position information.

6. A three-dimensional position calibration system for calibrating ultrasonic image data generated by a probe that emits ultrasonic waves onto an object under test and receives reflections of said ultrasonic waves from said object under test, said probe having a magnetic receiver attached thereto for receiving a magnetic field generated by a magnetic transmitter in order to detect a three-dimensional spatial coordinate of said probe from said object under test, said three-dimensional position calibration from comprising:

a calibrator body;

a probe mounting board for attaching said probe to said calibrator body;

a base board for supporting said calibrator body and said magnetic field transmitter, said base board having a top surface; and a block disposed on said top surface of said base board capable of securing said calibrator body in one of at least three different axial directions from said magnetic field generated by said magnetic transmitter.

7. The three-dimensional position calibration system according to claim 6, wherein said calibrator body is L-shaped, wherein said calibrator body has an upper, probe mounting, section and a lower section shaped as a horizontal rectangular to box.

8. The three-dimensional position calibration system according to claim 7, wherein said lower section of said calibrator body contains an elongated-hole-shaped reference target horizontally disposed at a predetermined height from a bottom surface of said lower section, for detection by the probe as a spatial virtual center.

9. The three-dimensional position calibration system according to claim 8, wherein said probe mounting board has a rubber plate mounted on a front surface of said probe mounting board, said rubber plate for protecting and preventing shifting of said probe, and said probe mounting board further has a metallic plate mounted on a rear surface of said probe mounting board, and wherein said probe mounting board is adjustably connected to said upper, probe mounting, section of the calibrator body.

10. The three-dimensional position calibration system according to claim 9, wherein said calibrator body is made of acrylic resin.

11. The three-dimensional position calibration system according to claim 10, wherein said three different axial directions are orthogonal from each other.

12. The three-dimensional position calibration system according to claim 11, wherein said lower section of said calibrator body further contains a pair of axial reference targets vertically disposed on opposite sides of said elongated-hole shaped reference target, for confirming whether the probe is positioned on a predetermined direction by ultrasonic image detection of said axial reference targets.

* * * * *